United States Patent

Crankshaw

[11] Patent Number: 5,879,360
[45] Date of Patent: Mar. 9, 1999

[54] SYRINGE PUMPS

[75] Inventor: David Pilkington Crankshaw, Toorak, Australia

[73] Assignee: The University of Melbourne, Parkville, Australia

[21] Appl. No.: 687,349

[22] PCT Filed: Jan. 20, 1995

[86] PCT No.: PCT/AU95/00029

§ 371 Date: Sep. 16, 1996

§ 102(e) Date: Sep. 16, 1996

[87] PCT Pub. No.: WO95/20145

PCT Pub. Date: Jul. 27, 1995

[30] Foreign Application Priority Data

Jan. 21, 1994 [AU] Australia ................. PM3485

[51] Int. Cl.$^6$ .................................................. A61M 5/00
[52] U.S. Cl. ............................................................. 606/154
[58] Field of Search ............................... 604/65, 67, 151, 604/152, 154, 155; 128/DIG. 1, DIG. 12, DIG. 102; 73/718, 724

[56] References Cited

U.S. PATENT DOCUMENTS

| | | |
|---|---|---|
| 2,707,954 | 5/1955 | Kas, Sr. . |
| 3,122,281 | 2/1964 | Damgaard . |
| 3,678,378 | 7/1972 | Trott et al. . |
| 4,275,383 | 6/1981 | White et al. . |
| 4,384,496 | 5/1983 | Gladwin . |
| 4,448,085 | 5/1984 | Lee . |
| 4,463,614 | 8/1984 | Lee . |
| 4,584,625 | 4/1986 | Kellogg . |
| 4,629,957 | 12/1986 | Walters et al. . |
| 4,652,260 | 3/1987 | Fenton, Jr. et al. . |
| 4,815,313 | 3/1989 | Beard . |
| 4,862,743 | 9/1989 | Seitz . |
| 5,232,449 | 8/1993 | Stern et al. . |
| 5,235,324 | 8/1993 | Gagnebin . |

FOREIGN PATENT DOCUMENTS

| | | |
|---|---|---|
| 47513/79 | 12/1979 | Australia . |
| 24839/84 | 8/1984 | Australia . |
| 72648/87 | 11/1988 | Australia . |
| 276474 | 8/1988 | European Pat. Off. . |
| 376632 | 7/1990 | European Pat. Off. . |
| 380885 | 8/1990 | European Pat. Off. . |
| 783520 | 4/1935 | France . |
| 882743 | 3/1943 | France . |
| 1419205 | 10/1965 | France . |
| 1445659 | 6/1966 | France . |
| 2308923 | 11/1976 | France . |
| 1473543 | 6/1962 | Germany . |
| 1909979 | 9/1969 | Germany . |
| 1285762 | 8/1972 | United Kingdom . |

*Primary Examiner*—William Lewis
*Attorney, Agent, or Firm*—Andrus, Sceales, Starke & Sawall

[57] ABSTRACT

A syringe pump having a drive head (1) mounted on a lead screw (2) which drives the drive head (1) to cause the plunger (P) of the syringe (S) to be advanced to deliver the contents of the syringe in a controlled manner. The drive head (1) supports a sensing module (3) having a cylindrical outer metallic body supporting a sensor disk (9) to which a sensing button (10) is attached. The disk (9) has a central insulating disk (15) supporting copper plates (16 and 17) and thin layers of dielectric (18, 19) separated from ground plates (20, 21) by an air gap (22) defining separate electrical capacitors each having a significantly different value of capacitance such that a large fall in capacitance occurs in the first capacitor while a large rise in capacitance occurs in the second capacitor. The capacitors are connected to an integrated circuit (23) which detects changes in capacitance caused by small forces applied to the button (10) to provide signals representative of contact with the button (10) and/or the force applied by the button (10) and the plunger (P). The drive head (1) also carries spring loaded pawls (26, 27) which engage behind the flange of the plunger (P) of the syringe (S) to prevent plunger movement caused by siphoning or other undesired movement of the plunger.

15 Claims, 2 Drawing Sheets

SYRINGE PUMPS

FIELD OF THE INVENTION

This invention relates to improvements in infusion devices and more particularly to improvements to the drive head of a syringe pump.

BACKGROUND OF THE INVENTION

Various forms of syringe pump are commercially available and have been proposed in the patent literature. Examples of such patent literature include our own patents, such as U.S. Pat. Nos. 4,741,732 Crankshaw et al and 5,034,994 Crankshaw et al.

A head switch which operates when the drive head or pusher makes contact with the plunger flange of the syringe is required to permit:

(1) Sizing of syringes by identifying correct engagement of the drive head in the empty and filled positions to permit calculation of the internal volume of the syringe from data entered by the operator;

(2) Identification of operator interference with the drive head;

(3) Detection of separation of the syringe plunger from the drive head, which may occur with spontaneous delivery of fluid, or siphoning, from the syringe in excess of that caused by the pusher;

(4) Disengagement of the drive head and hence depressurisation of the contents of the syringe prior to the sounding of an occlusion alarm.

In each of the above patents, a conventional microswitch with dual contacts was utilized. While such switches are reliable, it is necessary to incorporate a small lever to reduce the actuating force to the 10 to 20 gram range. A force above 10 gram is necessary to avoid spurious actuation if the position of the syringe pump is changed suddenly. On the other hand the actuating force must be less than 20 gram so that the plunger of a small syringe is not operated by the switch before contact has been sensed. Even with the smallest switch available, the lever must travel an excessive distance before the switch operates. This leads to unacceptable delays in sensing the contact or the release of the pusher with the drive head. A further disadvantage of a microswitch is the difficulty of rendering it waterproof without considerably increasing the force necessary to operate it.

SUMMARY OF INVENTION AND OBJECTS

It is an object of a first aspect of the present invention to provide a sensor which operates as a means for sensing contact between a device for exerting a force and an object, such as the drive head or pusher of a syringe pump and the plunger of the syringe, in a mariner which ameliorates the above stated disadvantages.

In a first aspect, the invention provides a force sensor for a device which exerts a force on an object, comprising spaced conductive members, insulating means carrying conductive elements covered by dielectric materials to define with said conductive members a pair of capacitors, biasing means for maintaining one of said dielectric materials closely adjacent to or in contact with one of said conductive members, the other conductive member being spaced to define an air gap between the other dielectric material and the other conductive member, means for applying a contact force to said insulating means to move said insulating means towards said other conducting member to close said air gap to thereby change the capacitance of one of said capacitors, and means for utilizing said change in capacitance to detect the application of said force to said sensor.

In one form of the invention, the sensor is a contact sensor capable of detecting forces between about 10 and 20 grams, and in this form, the air gap is small and the biasing means requires only a small force of about 10 grams to cause movement of the insulating means to close the air gap.

The insulating means is preferably in the form of an insulating disk having conductive plates, such as copper plates, fixed to its opposite surfaces with a thin dielectric layer overlying the conductive plates. A small spring supplies the biasing force which holds the dielectric on one side of the insulating disk in engagement with one of the conductive members thereby leaving a small air gap between the other dielectric covering and the other conductive member. An actuating button is secured to the disk and the assembly is mounted in the drive head or pusher of a suitable syringe pump.

Syringe pumps often include a force sensing transducer which measures the force applied by the drive head or pusher to the syringe plunger. The need to know the force applied to the syringe plunger is primarily for the purpose of detecting fluid blockages, as evidenced by a force exceeding a predetermined value, or other events, such as jamming of the syringe plunger, which prevent the desired infusion of the contents of the syringe.

Force transducers suitable for measuring forces in the operating range of 20 to 5,000 grams are available commercially but they have major disadvantages in the present application. In general they are complex and hence expensive, involving piezo electric or resistive transducers. Such devices operate at very low signal levels requiring amplification. This adds complexity and the low level of electrical operation is sensitive to interference by external magnetic or electrostatic fields.

In a second aspect of the invention, there is provided a force transducer for a device which exerts a force on an object, comprising a first conductive member and a second conductive member defining plates of a capacitor, a dielectric material interposed between the plates, means for biasing the dielectric material in contact with the first conductive member, and means for mounting the second conductive member for movement with respect to the first conductive member to create an increasing air gap between said capacitor plates which changes the capacitance of the capacitor in proportion to the force applied to cause movement of said second conductive member with respect to the first, the first conductive member forming part of a conductive body within which a force detecting member is mounted for movement against the action of a biasing spring, the second conductive member being attached to the force detecting member so as to be adjacent the first conductive member in the rest position. Thus as the force detecting member is moved by the application of the force, the second conductive member moves away from the first conductive member and is separated by an increasing air gap which causes the capacitance of the capacitor to change in a manner proportional to the applied force.

In a particularly preferred form, the first and second aspects defined above are included in a syringe pump, or in some other force applying means. The change in the capacitance in each device can be used as a "fail safe" means of detecting that a force is being applied by the drive head or other force applying means equivalent to the dual contact microswitch of the prior art. In the embodiment described, detection of an increase in capacitance of one of the capacitors of the contact sensor as well as a reduction in capacitance of the force transducer confirms that operation of the device has in fact occurred.

Another issue relevant to syringe pumps is the prevention of siphoning. If a syringe is connected via a long delivery tube to an open vein in a patient and elevated above the body of the patient, there is a danger that the force of gravity to cause the syringe to discharge its contents. This is a particular problem with syringe pumps placed on shelves above a patient, such as the top of an anaesthesia machine, or when they are attached to a pole used for hanging intravenous solutions.

Mechanical systems to prevent siphoning have been constructed in a variety of ways in other devices for the automatic delivery of drug. A frequent solution is to incorporate a fixed hook on the drive head, requiring the operator to engage the flange of the syringe plunger for it to function correctly (TERUMO, ATOM). This approach requires the operator to correctly engage the flange. If the operator fails to do this the error may not be detected and inadvertent siphoning of the contents of the syringe may occur.

Alternatively, a clamping mechanism is incorporated in the mechanism of the drive head to clamp the flange of the syringe plunger when the lead screw of the drive mechanism is engaged (IVAC 770). This approach usually limits the range of sizes of syringe that can be clamped. The method also relies on the operator to correctly engage the clamp.

A further method, which is widely used, is a separate clamping mechanism, which forcibly holds the syringe plunger against the pusher or drive head and which is described in U.S. Pat. No. 5,232,449.

In some devices a switch is actuated to identify correct engagement of the plunger (IVAC 770) and described in U.S. Pat. No. 5,232,449.

A further approach to the problem of engaging the plunger of the syringe in the drive head is to employ a set of hooks which surround the flange and toggle as the flange is engaged. This type of approach (BAXTER) has several disadvantages:

(1) It is suitable only for syringes where the diameter of the flange is relatively constant.

(2) They do not permit removal of the syringe from the clamp unless the hooks are disengaged.

(3) The construction by its nature is relatively weak as the hooks must be attached to the drive head at a number of points around the circumference of the drive head and are likely to be broken as the syringe is removed from the pump in an incorrect manner.

The infusion pumps described in our U.S. patents did not incorporate a mechanical plunger restraining mechanism. One reason for this was that a syringe plunger restraining mechanism would restrict the automatic operation of the pusher in sizing syringes, automatically engaging the drive head and most particularly in detecting removal of the force of the pusher on the plunger of the syringe when an occlusion had been detected.

It is the object of a third aspect of the present invention to provide a simple but effective means for preventing undesired movement of the syringe plunger to thereby prevent siphoning.

In a third aspect of the invention, there is provided a means for preventing undesired movement of a plunger of a syringe in a syringe pump having a drive head or pusher adapted to engage the syringe plunger, comprising one or more pawls carried by the drive head and biased to engage the plunger head when engaged with the drive head to prevent movement of said plunger with respect to said drive head in a dispensing direction.

A multiplicity of pawls are preferably provided at different positions on the drive head to ensure that all syringe sizes are engaged and that redundancy is present.

Since the pawls are carried by the drive head, movement of the drive head into engagement with the plunger is not impeded and only movement of the plunger with respect to the drive head is prevented. Thus, in this simple and inexpensive way, siphoning is prevented.

BRIEF DESCRIPTION OF THE DRAWINGS

One presently preferred form of the invention will now be described with reference to the accompanying drawings in which.

DESCRIPTION OF PREFERRED EMBODIMENT

Embodiments of each of the above aspects of the invention are described in relation to devices suitable for use with syringe pumps of the general type described in the U.S. patents referred to above. The contents of the specifications of these patents are incorporated into the present specification by cross reference. Since the details of the syringe pump other than those described below are not necessary for an understanding of the present invention, they will not be further described and the reader is directed to the specifications of the U.S. patents for further information concerning the syringe pump structure and operation.

Figure 4:
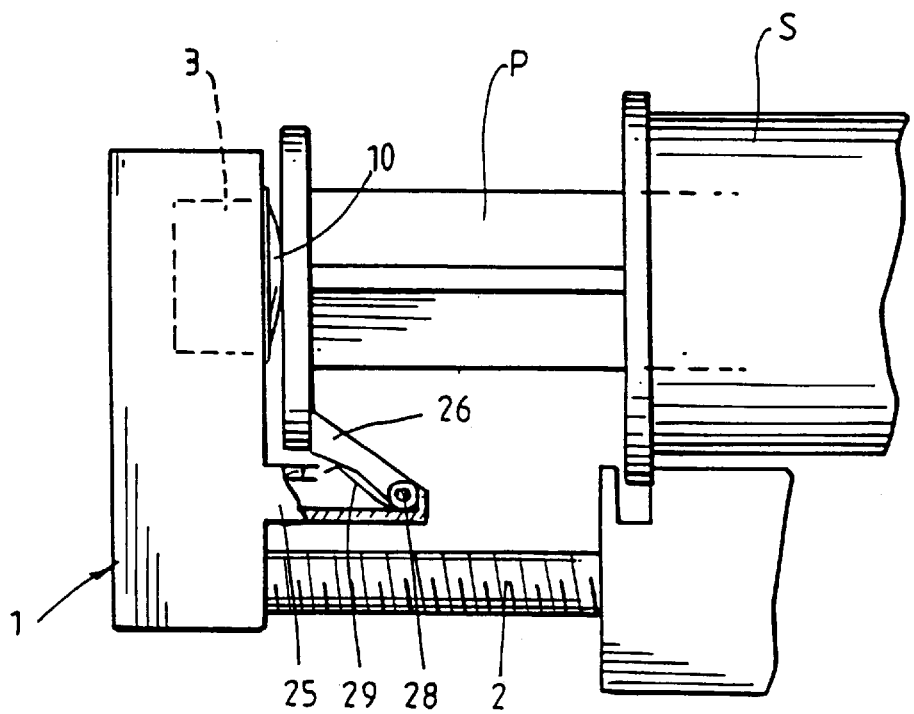
FIG. 4 is a fragmentary elevation of the syringe pump of FIG. 3 showing the pawls engaging the plunger of a syringe.

As shown in FIG. 4 of the drawings, the syringe pump has a drive head or pusher 1 mounted on a lead screw 2 which drives the drive head 1 to cause the plunger P of the syringe shown in FIG. 4 to be actuated to deliver the contents of the syringe S in a controlled manner. The drive head 1 supports a sensing module 3, which is shown in greater detail in FIGS. 1, 2 and 2A of the drawings, and the sensing module will now be further described.

Figure 1:
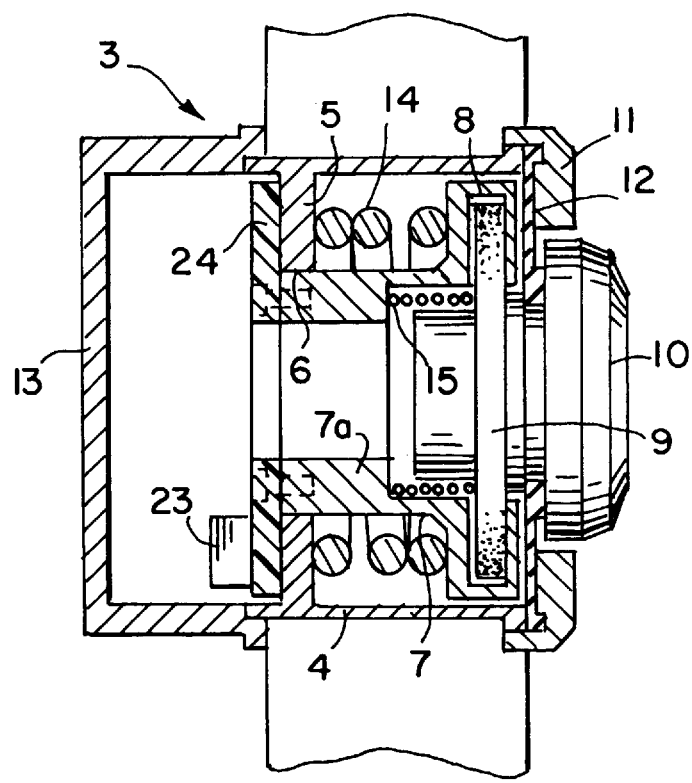
FIG. 1 is a sectional elevation of the contact sensing and force detecting portion of the drive head of a syringe pump.

As shown in FIG. 1, the sensing module 3 comprises an outer metallic body 4 of generally cylindrical form having an inwardly directed annular flange 5 defining a central passage 6 through which a cylindrical portion 7a of an inner body 7 passes as a sliding fit. The inner body is also formed with an annular cavity 8 which receives the edge of a disk 9 to which button 10, of insulating material such as nylon or some other suitable plastic, is attached. The outer body 4 is closed at the front by the button and a surrounding cap 11 which holds a silicone rubber seal 12 in place. The other end of the outer body 4 is closed by an end cap 13.

A compression spring 14 is positioned between the inner body 7 and the flange 5 of the outer body 4 and a further small spring 15 is positioned between the portion 7a of the inner body and the disk 9.

Figure 2A:
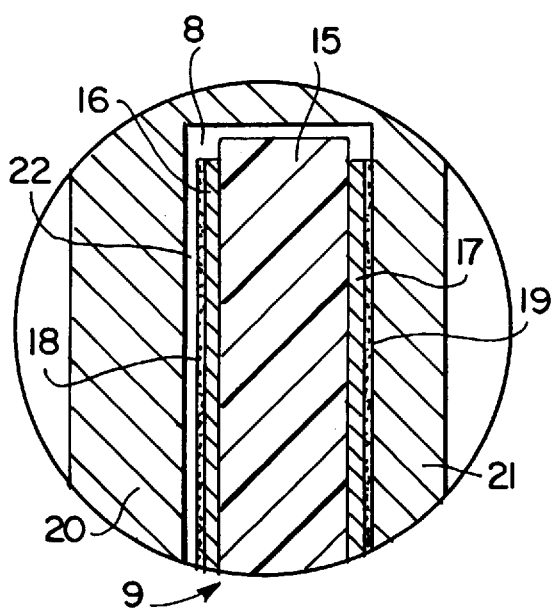
FIG. 2A is an enlarged fragmentary sectional elevation of the indicated portion of the contact sensor of the sensing module of FIG. 2.
Figure 2:
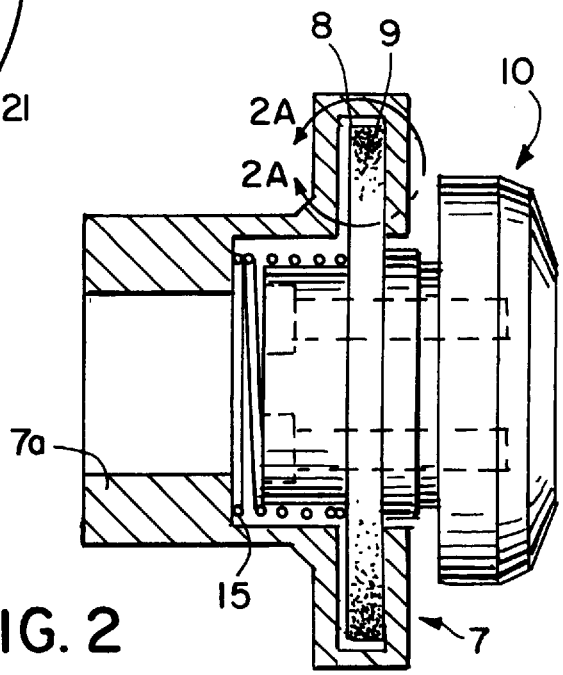
FIG. 2 is an enlarged sectional elevation of the contact sensing module of FIG. 1.

Referring now to FIGS. 2 and 2A, the contact sensor of the sensing module 3 is shown in greater detail. It will be noted from FIG. 2 that the disk 9 comprises a central insulating disk 15 having copper plates 16 and 17 secured to either face, with a thin layer of dielectric 18, 19 applied over each copper plate 16, 17. The walls defining the cavity 8 in the inner body are in the form of conductive ground plates 20, 21 and the spacing between the plates 20, 21 is such that a small air gap 22 exists between the dielectric 18 and the ground plate 20, the other dielectric 19 being held in contact with the ground plate 21 by means of the spring 15.

Wires (not shown) are connected separately to the ground plates 20, 21 and to each of the copper plates 16, 17 and the wires are connected to an integrated circuit 23 (FIG. 1). It will be appreciated that the ground plates 20, 21 and the copper plate 16, 17 define two separate electrical capacitors each having a significantly different value of capacitance. The first capacitor defined by the copper plate 17, the round plate 21 and the intervening dielectric 19 has a relatively high capacitance dominated by the dielectric material 19. The second capacitor includes the air gap 22 and it therefore has a considerably lower capacitance. Thus, as the button 10 is moved to the left against the action of the spring 15 by contact with the plunger of a syringe, the dielectric 18 comes into contact with the ground plate 20 closing the air gap 22 and creating a similar air gap between the dielectric 19 and the ground plate 21. Thus, a large fall in capacitance occurs in the first capacitor while a large rise in capacitance occurs in the second capacitor.

The size of the spring 15 and the dimensions of the air gap 22 are selected to provide the required characteristics suitable for the syringe pump in question. In general, a change in capacitance by a factor of two can be produced by a force in the range of 10 to 20 grams with a movement of less than 0.5 millimeters.

In the present embodiment, the integrated circuit 23 to which the capacitors are connected is a Motorolla MM74HC14M which is configured so that pulses emitted from the integrated circuit 23 have a frequency which is inversely proportional to the capacitance of the contact sensor. The integrated circuit 23 is preferably mounted within the sensing module 3 to render the low current flows produced by the changes in capacitance relatively immune from outside electrical interference. The signals emitted by the integrated circuit 23 comprise a series of voltage pulses (of about 5 volts amplitude), the frequency of which may be determined directly by interval measurement or by conversion to a variable voltage by appropriate frequency measuring circuitry (not shown). As described above, this results in two channels of information signifying that a syringe has made contact with the button 10.

The sensing module 3 also incorporates a force transducer, which in this embodiment is separate from the contact sensor described above. The force transducer comprises a two plate capacitor with an air gap, one plate of the capacitor being defined by the annular flange 5, and the other plate being defined by an insulating disk 24 secured to the free end of the cylindrical portion 7a of the inner body 8 in the manner shown in FIG. 1. The disk 24 has a copper plate and overlying dielectric (not shown) formed on the face adjacent to the annular flange 5, and when the button 10 is forced to the left by contact with the syringe plunger, the applied force causes the disk 24 to move away from the annular flange 5 as the spring 14 is compressed. This results in a decrease in the capacitance of the force transducer capacitor as the air space increases, and since the increase in the air gap is proportional to the force applied to the button 10, the change in the capacitance of this capacitor is a measure of the force applied. The plates of this capacitor are similarly connected to the integrated circuit 23 and the change in capacitance is detected in the manner similar to that described above.

The capacitance of the force transducer capacitor may be influenced by the humidity or amount of water vapour present in the air. To compensate for this, the two capacitors in the contact sensor described above may be used. Using the control computer (not shown) of the syringe pump to sense the frequency of the signal train from the contact capacitors, it can be determined that one capacitor is in the closed position and that the air has been excluded. If this is so, and due to the interconnection between the capacitors, the other capacitor will have an air gap of known dimensions. The frequency resulting from this air gap will then mainly be dependent on the humidity of the air in the gap. The frequency from this capacitor can be used as a correction signal for the force transducer capacitor because it utilizes the same air.

In addition, the signal from the first capacitor of the contact sensor and the signal from the force transducer can be used to provide a further "fail safe" method of detecting operation of the syringe pump.

Figure 3:
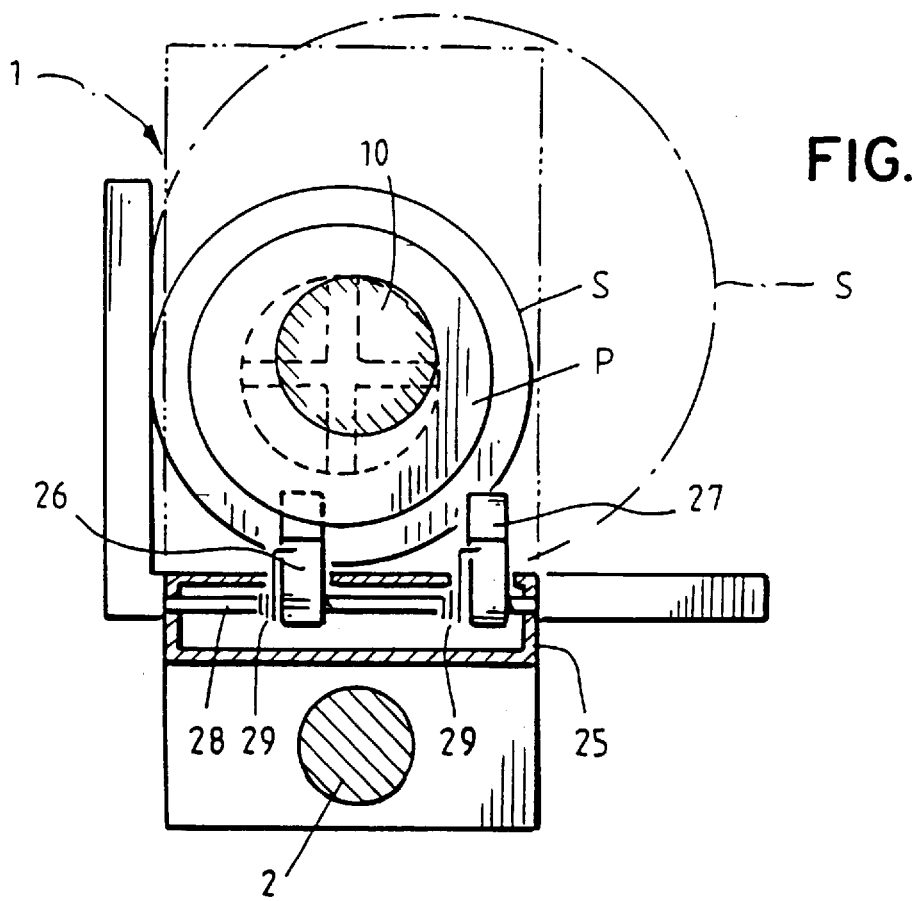
FIG. 3 is a sectional end elevation of a syringe pump showing the siphon preventing pawls.

Referring now to FIGS. 3 and 4 of the drawings, the preferred mechanism for preventing siphoning will now be described. The device includes a robust mounting block 25 protruding from the base of the drive head 1 in the manner shown in FIGS. 3 and 4. Two or more syringe plunger flange engaging pawls 26, 27 are pivotally mounted on a pivot pin 28 within the mounting block 25, with the pawls 26,27 projecting through openings in the mounting block 25. Each pawl 26, 27 is lightly loaded by a small spring 29 to prevent the plunger flange moving past the pawl 26, 27 as a result of siphoning or other undesired movement of the plunger. The pawls 26, 27 are easily displaced against the action of the spring 29 by insertion of the plunger flange into the drive head and the distance between the button 10 of the drive head sensing module 3 and the pawls 26, 27 is enough to permit movement of the plunger flange so that the contact sensor can engage and disengage.

The mounting block 25 is set level to the floor of the syringe cradle (FIG. 3) and has a sloping front surface to ensure that a plunger falling slightly below the level of the floor of the syringe cradle is guided up to meet the pawl 26 or 27 as the drive head 1 moves forward to engage the plunger flange. The mounting block 25 is preferably open from below to permit free drainage and to facilitate cleaning and reduce the risk of jamming.

The mounting block 25 could optionally be right angled conforming to the shape of the syringe cradle and this may facilitate the clamping of smaller syringes.

It will be noted from FIG. 3 of the drawings that the two pawls 26, 27 shown will prevent undesired movement of the plunger flange of the smallest and largest syringe respectively. If desired, further pawls may be provided to ensure that plungers in syringes of all dimensions may be clamped.

I claim:

1. A syringe pump comprising:
   means for holding a syringe;
   a drive head for a plunger of the syringe held by said holding means, said drive head including sensor means, said sensor means being further defined as a sensor for sensing the exertion of force by the drive head on the plunger of the syringe, and wherein said coupling means is further defined as coupling said insulating means to a device engaging the plunger for altering the position of said insulating means in the space responsive to the exertion of force on the syringe plunger by the device.

2. The syringe pump according to claim 1 further comprising means for preventing undesired movement of the plunger in the syringe, said means comprising one or more pawls carried by said by drive head and biased to engage the plunger when the plunger is engaged with the drive head to prevent movement of the plunger with respect to the drive head in a dispensing direction.

3. A syringe pump comprising:

means for holding a syringe;

a drive head for moving a plunger of the syringe held by said holding means, said drive head including a force transducer, said force transducer being further defined as a force transducer for sensing the amount of force exerted on the plunger of the syringe, and wherein said force detecting member is further defined as coupled to a device engaging the plunger for creating a gap between said first and second conductive members responsive to the exertion of force on the syringe plunger by the device to move the plunger.

4. The apparatus according to claim 3 further comprising means for preventing undesired movement of the plunger in the syringe, said means comprising one or more pawls carried by said by drive head and biased to engage the plunger when the plunger is engaged with the drive head to prevent movement of the plunger with respect to the drive head in a dispensing direction.

5. A sensor for sensing the exertion of force by a device on an object, said sensor comprising:

a pair of electrically conductive members mounted in said sensor and separated from each other by a space;

an insulating means positioned in the space and between said conductive members, said insulating means having a first surface facing one of said conductive members and a second surface facing the other of said conductive members, said first and second surfaces each carrying an electrically conductive element covered by dielectric material for defining, with the adjacent conductive member, a pair of capacitors in said sensor;

biasing means coupled to said insulating means for positioning said insulating means in the space such that the dielectric material on said first surface is contiguous with the adjacent conductive member and the dielectric material on said second surface is spaced from the adjacent conductive member by an air gap;

means coupling said insulating means to the device for altering the position of said insulating means in the space responsive to the exertion of force on the object by the device to close the air gap between said dielectric material on said second surface and said adjacent conductive member, thereby to change the capacitance of the capacitor formed by these components; and means responsive to said change in capacitance to detect the exertion of force on the object by the device.

6. The sensor of claim 5 wherein said insulating means is formed of an insulating disk having conductive plates fixed to said first and second surfaces with a thin dielectric layer overlying each of the conductive plates.

7. The sensor of claim 3 wherein said conductive plates comprise copper plates.

8. The sensor of claim 5 wherein said biasing means comprises a spring.

9. The sensor of claim 5 wherein said force sensor is further defined as capable of sensing the exertion of a force of about 10 to 20 grams and wherein said biasing means is further defined as allowing the exertion of a force of about 10 grams to cause said coupling means to alter the position of said insulating means in the space.

10. The sensor of claim 9, wherein said insulating means is formed of an insulating disk having conductive plates fixed to said first and second surfaces with a thin dielectric layer overlying each of the conductive plates.

11. The sensor of claim 5 wherein the position of said insulating means in the space is altered responsive to the exertion of force to open an air gap between said dielectric material on said first surface of said insulating means and its adjacent conductive member, thereby to change the capacitance of the capacitor defined by these components in a manner that is opposite to the manner in which the capacitance of the capacitor defined by the second surface of said insulating means and its adjacent conductive member is changed.

12. The sensor of claim 5 further defined as a sensor for sensing the exertion of force by a syringe pump drive head on a syringe plunger.

13. A force transducer for sensing the amount of force exerted by a device on an object, said transducer comprising:

a body;

a force detecting member movably mounted within said body, said force detecting member being coupled to the device;

a first electrically conductive member mounted on said body;

a second electrically conductive member mounted on said force detecting member, said first and second conductive members being juxapositioned with respect to each other to define opposing plates of a capacitor;

dielectric material interposed between said first and second conductive members;

biasing means for biasing said first and second conductive members together with said dielectric material in between, said force detecting member and said second conductive member being movable against the bias of said biasing means responsive to the exertion of force on the object by the device to create an air gap between said first and second conductive members which changes the capacitance of the capacitor defined by said members in proportion to the force exerted by the device on the object; and means responsive to said change in capacitance to detect the amount of force exerted by said device on said object.

14. The force transducer according to claim 13 wherein said biasing means comprises a biasing spring.

15. The force transducer of claim 13 further defined as a force transducer for sensing the amount of force exerted by a syringe pump drive head on a syringe plunger.

* * * * *